US011844853B2

(12) United States Patent
Pramanik et al.

(10) Patent No.: US 11,844,853 B2
(45) Date of Patent: Dec. 19, 2023

(54) ANTIPERSPIRANT COMPOSITION

(71) Applicant: Conopco, Inc., Englewood Cliffs, NJ (US)

(72) Inventors: Amitava Pramanik, Bangalore (IN); Satyajit Samadder, Bangalore (IN); Priyanka Sarkar, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/266,048

(22) PCT Filed: Jul. 22, 2019

(86) PCT No.: PCT/EP2019/069626
§ 371 (c)(1),
(2) Date: Feb. 4, 2021

(87) PCT Pub. No.: WO2020/030414
PCT Pub. Date: Feb. 13, 2020

(65) Prior Publication Data
US 2021/0308022 A1 Oct. 7, 2021

(30) Foreign Application Priority Data

Aug. 9, 2018 (EP) .................................. 18188280

(51) Int. Cl.
*A61K 8/27* (2006.01)
*A61K 8/04* (2006.01)
*A61K 8/34* (2006.01)
*A61K 8/36* (2006.01)
*A61K 8/41* (2006.01)
*A61Q 15/00* (2006.01)

(52) U.S. Cl.
CPC ................ *A61K 8/27* (2013.01); *A61K 8/046* (2013.01); *A61K 8/345* (2013.01); *A61K 8/36* (2013.01); *A61K 8/41* (2013.01); *A61Q 15/00* (2013.01); *A61K 2800/31* (2013.01); *A61K 2800/58* (2013.01); *A61K 2800/591* (2013.01)

(58) Field of Classification Search
None
See application file for complete search history.

(56) References Cited

U.S. PATENT DOCUMENTS

| 4,007,262 | A | 2/1977 | Bowers |
| 4,650,671 | A | 3/1987 | Golman |
| 4,915,939 | A | 4/1990 | Iwahashi |
| 2005/0238730 | A1 | 10/2005 | Le Fur et al. |
| 2014/0170086 | A1 | 6/2014 | Pan et al. |
| 2015/0313821 | A1 | 11/2015 | Yuan et al. |
| 2015/0313822 | A1 | 11/2015 | Pan et al. |
| 2016/0089315 | A1 | 3/2016 | Kleinberg et al. |

FOREIGN PATENT DOCUMENTS

| DE | 3808114 | 9/1989 |
| DE | 19962881 | 6/2001 |
| EP | 0586235 | 3/1994 |
| JP | 63277686 | 11/1988 |
| WO | WO 2008/148610 | * 12/2008 |
| WO | WO2008148610 | 12/2008 |
| WO | WO2013013903 | 1/2013 |
| WO | WO 2013/160092 | * 10/2013 |
| WO | WO2013160092 | 10/2013 |
| WO | WO2014098818 | 6/2014 |
| WO | WP2014098818 | 6/2014 |
| WO | WO2019110290 | 6/2019 |
| WO | WO2019206764 | 10/2019 |
| WO | WO2020030414 | 2/2020 |
| WO | WO2022029278 | 2/2022 |

OTHER PUBLICATIONS

Search Report and Written Opinion in EP18188280; dated Feb. 14, 2019; European Patent Office (EPO).
Search Report and Written Opinion in EP18188280.4; dated Feb. 14, 2019; European Patent Office (EPO).
Search Report and Written Opinion in PCTEP2019069626; dated Oct. 2, 2019.
Search Report and Written Opinion in EP19210354.7; dated May 14, 2020
Search Report and Written Opinion in EP20189795.6; dated Jan. 22, 2021.
B. B. Michniak; Studies on the mechanism of topical anhidrosis due to polyvalent cations; International Journal of Cosmetic Science; 1981; pp. 29-36; 3; Retrieved from Internet on Jan. 14, 2021.
Search Report and Written Opinion in PCTEP2020082342; dated Jan. 22, 2021
Search Report and Written Opinion in PCTEP2021071962; dated Nov. 5, 2021; World Intellectual Property Org. (WIPO).
Written Opinion 2 in PCT/EP2021/071962; dated Jul. 8, 2022; World Intellectual Property Org. (WIPO).
International Preliminary Report on Patentability in PCT/EP2021/071962; dated Sep. 26, 2022; World Intellectual Property Org. (WIPO).

* cited by examiner

*Primary Examiner* — Patricia Duffy
*Assistant Examiner* — Garen Gotfredson
(74) *Attorney, Agent, or Firm* — Greenberg Traurig, LLP

(57) ABSTRACT

The present invention is in the field of personal care compositions, in particular compositions comprising antiperspirant actives. The present invention more particularly relates to compositions which do not contain the conventional and well established aluminium based actives, yet exhibit similar efficacy. This is achieved through use of an active which is a complex of a zinc salt with a β amino acid in an anhydrous carrier.

13 Claims, No Drawings

ANTIPERSPIRANT COMPOSITION

RELATED APPLICATIONS

The present application is a national phase filing under 35 USC 371 of International Application No. PCT/EP2019/069626, filed on Jul. 22, 2019, which claims priority from European Patent Application No. 18188280.4, filed on Aug. 9, 2018, the contents of which are incorporated herein in their entirety for all purposes.

FIELD OF THE INVENTION

The present invention is in the field of compositions comprising antiperspirant actives, particularly cosmetic compositions. The present invention more particularly relates to compositions comprising zinc based antiperspirant actives which exhibit efficacy similar to or better than that of well known aluminium based actives.

BACKGROUND OF THE INVENTION

The present invention relates to compositions, such as those that contain antiperspirant actives. These actives are added to compositions to reduce perspiration on application to the surface of the body, particularly to the underarm regions of the human body viz. the axilla. Antiperspirant actives are typically astringent metal salts such as those of aluminium or zirconium salts. Antiperspirant actives are usually incorporated in compositions at low pH, in the range of 2 to 7. There has been a thrust to develop antiperspirant actives which are less astringent and the approach has been to look for actives that do not contain aluminium. The present inventors with their extensive research in the field of zinc compounds have hit upon a zinc compound which is a complex of a zinc salt with specifically β amino alcohol which is found to have similar or better efficacy as compared to that of well-established aluminium based actives.

Certain zinc salts have been reported as antiperspirant active. US2015313821 (Colgate) discloses an antiperspirant formulation comprising a protein and an antiperspirant salt which may be a zinc X halide complex where X is an amino acid or a trimethyl glycine. The present inventors have found that the efficacy of the zinc complex of the present invention is superior to that disclosed in this prior art.

The present inventors have tested the antiperspirant efficacy of the zinc complex of the present invention especially in an anhydrous carrier and found it to be similar to that obtained with traditional aluminium chlorohydrate while having lesser amount of astringency.

It is thus an object of the present invention to provide for an antiperspirant composition which exhibits high antiperspirant efficacy while having reduced astringency.

SUMMARY OF THE INVENTION

According to the first aspect of the present invention there is provided an antiperspirant composition comprising
(i) a complex of a zinc salt with a β amino alcohol; and
(ii) an anhydrous carrier,
wherein the molar ratio of zinc salt top amino alcohol is from 1:0.5 to 1:3

It is particularly preferred that the β amino alcohol is chosen from mono ethanol amine, diethanol amine, triethanol amine or 2-amino-1-butanol.

According to another aspect of the present invention there is provided a method of reducing perspiration comprising the step of applying a composition as claimed in the first aspect on to the desired skin surface.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The compositions of the invention are typically "personal care compositions", suitable for cosmetic use as detailed below. Further, use of the compositions of the invention is typically cosmetic, non-therapeutic use.

In some embodiments of the present invention, the compositions may be used for the therapeutic treatment of hyperhidrosis (extreme sweating).

By "An Antiperspirant Composition" as used herein, is meant to include a composition for topical application to the skin of mammals, especially humans. Such a composition is preferably of the leave-on type. By a leave-on composition is meant a composition that is applied to the desired skin surface and left on for a period of time (say from one minute to 24 hours) after which it may be wiped or rinsed off with water, usually during the regular course of personal washing. The composition may also be formulated into a product which is applied to a human body for improving the appearance, cleansing, odor control or general aesthetics. The composition of the present invention can be an anhydrous composition which could be in the form of a liquid, scrub, gel or stick form and may be delivered through a roll-on device or using an aerosol can which may contain a propellant. It is especially useful for delivering compositions to the axilla of an individual for anti-perspirancy benefits. "Skin" as used herein is meant to include skin on any part of the body where one may sweat (e.g., neck, chest, back, arms, underarms, hands, legs, buttocks and scalp) especially the underarms.

The present invention is directed to delivering a zinc based antiperspirant active on to the topical surface of a human body. The active for inclusion in the composition is a complex of a zinc salt with a β amino alcohol.

Suitable salt for use in preparing the complex are a chloride, formate, acetate, propionate, gluconate or citrate of zinc.

The preferred β amino alcohol for use in preparing the complex with the zinc salt is chosen from mono ethanol amine, diethanol amine, triethanol amine or 2-amino-1-butanol.

β amino alcohols have the structure as given below:

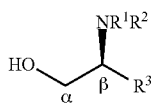

Where R1, R2 and R3 are an alkyl or aryl group which may be functionalized or is H.

When R1, R2 and R3 are functionalized, it is most preferably β-hydroxy or o-phenolic functionalized.

The structure of the preferred β amino alcohols are:

Monoethanol Amine (MEA)

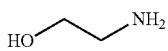

Diethanol Amine (DEA)

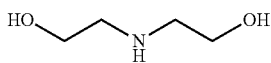

Triethanol Amine

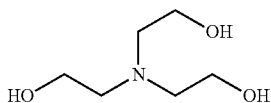

2-Amino-1-Butanol

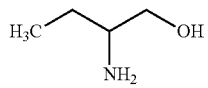

The present inventors have found that complexes of zinc salts only with β amino alcohols provide this benefit especially when incorporated in non-aqueous carriers. They found that this benefit is not found when α amino alcohol or γ amino alcohol are used. Without wishing to be bound by theory, the inventors believe that the complex when included in the anhydrous composition precipitates in the presence of water (available from sweat) to form a water insoluble compound. A typical example of this reaction is that when zinc acetate dihydrate ethanolamine complex is brought in contact with water it forms a precipitate which is zinc hydroxy acetate which is an insoluble compound. This precipitate could then occlude the sweat pores thereby acting as an effective antiperspirant active.

The present inventors understood through their experimentation that such a reaction to form an insoluble precipitate occurs only when the complex is formed with a β amino alcohol. If one tries to use an α amino alcohol, the inherent stability of these alcohols makes it very difficult to prepare the complexes. When a γ-amino alcohol is used, the complex thus formed does not form an insoluble product when in contact with water thereby not forming an active that can behave as an anti-perspirant.

The complex is so included that the amount of zinc is preferably from 0.2 to 2%, more preferably from 0.5 to 1.5% by weight of the composition.

The zinc compound and the β amino acid are complexed in a molar ratio in the range of 1:0.5 to 1:3, preferably in the range of 1:1 to 1:3. The present inventors have found that the desired precipitation of the complex in aqueous media of sweat is good when the molar ratio is in the claimed range, thereby providing the desired AP activity.

The pH of the composition is preferably in the range of 5 to 8. The present inventors have found that when the pH of the composition is lowered below 5 or increased above 8, the zinc complex of the invention is likely to be more solubilized in the aqueous medium of the sweat thereby making the plugging of the sweat pores difficult. Under such conditions, the anti-perspirant activity is likely to be low. Therefore a pH in the range of 5 to 8 is preferred.

The complex is preferably prepared by a process comprising the steps of (i) dissolving the β amino alcohol in a volatile alcohol; and (ii) dissolving therein the zinc salt. It is preferred that the dissolution is carried out near room temperature i.e. from about 20° C. to about 40° C. The dissolution is preferably carried out in each of the individual steps for about 5 minutes to 30 minutes. Further preferably the solution of the complex is mixed to ensure complete dissolution from 1 hour to about 8 hours. It is preferred that the volatile alcohol is ethanol or propanol preferably ethanol. It is further preferred that a polyol preferably glycerol is included by dissolving it in the volatile alcohol to ensure better storage stability of the complex therein. The polyol, when used, is included in 0.1 to 2 wt % of the ethanolic solution.

The complex so prepared is preferably dissolved or suspended in an anhydrous solvent during the preparation of the composition of the invention. The anhydrous solvent is preferably selected from one or more of isopropyl alcohol, ethanol, silicone oil or polyhydric alcohol. Polyhydric alcohol is the most preferred anhydrous solvent for inclusion in the composition of the invention. It is also referred to in short as polyol. A polyhydric alcohol as per the present invention is a compound having two or more hydroxyl groups. Suitable class of polyhydric alcohols that may be included in the composition of the invention are monomeric polyols, polyalkylene glycols or sugars. Preferred monomeric polyols are glycol, propylene glycol, glycerol or xylitol. The anhydrous solvent is most preferably glycerol.

Antiperspirant compositions of the present invention may advantageously comprise an additional, non-zinc based antiperspirant active. Whilst this might be a conventional antiperspirant salt comprising Al and/or Zr, such as aluminium chlorohydrate or aluminium-zirconium chlorohydrate optionally complexed with glycine, it is preferred that any additional antiperspirant active is not of this type.

Other components commonly included in conventional antiperspirant compositions may also be incorporated in the compositions of the present invention. Such components include skin care agents such emollients, humectants and skin barrier promoters; skin appearance modifiers such as skin lightening agents and skin smoothing agents; antimicrobial agents, in particular organic anti-microbial agents, and preservatives.

The anti-perspirant active can be applied cosmetically and topically to the skin, broadly speaking, by one of two methods. Different consumers prefer one method or the other. In one method, sometimes called a contact method, a composition is wiped across the surface of the skin, depositing a fraction of the composition as it passes. In the second method, sometimes called the non-contact method, the composition is sprayed from a dispenser held proximate to the skin, often in an area of about 10 to 20 cm$^2$. The spray can be developed by mechanical means of generating pressure on the contents of the dispenser, such as a pump or a squeezable sidewall or by internally generated pressure arising from a fraction of a liquefied propellant volatilising, the dispenser commonly being called an aerosol.

There are broadly speaking two classes of contact compositions, one of which is liquid and usually applied using a roll-on dispenser or possibly absorbed into or onto a wipe, and in the second of which the antiperspirant active is distributed within a carrier liquid that forms a continuous phase that has been gelled. In one variation, the carrier fluid comprises a solvent for the antiperspirant and in a second variation, the antiperspirant remains a particulate solid that is suspended in an oil, usually a blend of oils.

Stick or Soft Solid Compositions

Many different materials have been proposed as gellant for a continuous oil phase, including waxes, small molecule gelling agents and polymers. They each have their advantages and of them, one of the most popular class of gellant has comprised waxes, partly at least due to their ready availability and ease of processing, including in particular linear fatty alcohol wax gellants. A gelled antiperspirant composition is applied topically to skin by wiping it across and in contact with the skin, thereby depositing on the skin a thin film.

The nature of the film depends to a significant extent on the gellant that is employed. Although wax fatty alcohols have been employed as gellant for many years, and are effective for the purpose of gelling, the resultant product is rather ineffective at improving the visual appearance of skin, and in particular underarm skin, to which the composition has been applied. This problem has been solved by including ameliorating materials for example, di or polyhydric humectants and/or a triglyceride oil.

Roll-on

Liquid compositions that are applicable from a roll-on broadly speaking can be divided into two classes, namely those in which an antiperspirant active is suspended in a hydrophobic carrier, such as a volatile silicone and those in which the antiperspirant active is dissolved in a carrier liquid. The latter has proven to be more popular. There are mainly two sorts of dissolving carrier liquid, namely carriers that are predominantly alcoholic, which is to say the greater part of the dissolving carrier fluid comprises ethanol and the second class in which the carrier liquid is mainly water. The former was very popular because ethanol is a mild bactericide in its own right, but its popularity waned because it stings, especially if the surface onto which the composition has been applied has been damaged or cut, such as can easily arise during shaving or other de-hairing operations.

The second class of formulations that is an alternative to alcoholic formulations comprise a dispersion of water-insoluble or very poorly water soluble ingredients in an aqueous solution of the antiperspirant. Herein, such compositions will be called emulsions. Antiperspirant roll-on emulsions commonly comprise one or more emulsifiers to maintain a distribution of the water-soluble ingredients.

Aerosol Compositions

The antiperspirant composition may be delivered through an aerosol composition which may comprise a propellant in addition to the other ingredients described hereinabove. Commonly, the propellant is employed in a weight ratio to the base formulation of from 95:5 to 5:95. Depending on the propellant, in such aerosol compositions the ratio of propellant to base formulation is normally at least 20:80, generally at least 30:70, particularly at least 40:60, and in many formulations, the weight ratio is from 90:10 to 50:50. A ratio range of from 70:30 to 90:10 is sometimes preferred.

Propellants herein generally are one of three classes; i) low boiling point gasses liquified by compression, ii) volatile ethers and iii) compressed non-oxidising gases.

Class i) is conveniently a low boiling point material, typically boiling below −5° C., and often below −15° C., and in particular, alkanes and/or halogenated hydrocarbons. This class of propellant is usually liquefied at the pressure in the aerosol canister and evaporates to generate the pressure to expel the composition out of the canister. Examples of suitable alkanes include particularly propane, butane or isobutane. The second class of propellant comprises a very volatile ether of which the most widely employed ether hitherto is dimethyl ether. This propellant can advantageously be employed at relatively low weight ratio of propellant to base formulation, for example to as low as 5:95. It can also be employed in admixture with, for example, compressible/liquefiable alkane gasses. The third class of propellant comprises compressed non-oxidising gasses, and in particular carbon dioxide or nitrogen. Inert gases like neon are a theoretical alternative.

When the composition of the invention is delivered in a roll-on, a firm solid or a stick format, the topically acceptable carrier comprises a hydrophobic carrier or an aqueous carrier. The hydrophobic carrier in such cases may comprise a silicone compound, low boiling alcohol or a wax. When the composition comprises a propellant it is delivered as an aerosol.

The composition of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, conditioners, exfoliating agents, pH adjusters, preservatives, natural extracts, essential oils, skin sensates, skin soothing agents, and skin healing agents.

The present invention also provides for a method of reducing perspiration comprising the step of applying the composition of the first aspect on to the desired skin surface. The skin surface could be any topical surface which is prone to sweating especially the axilla i.e. the underarm portion of the human body. The method is preferably non-therapeutic. The invention also provides for use of a complex of a zinc salt with a 8 amino alcohol for manufacture of a composition of the present invention, for reduction of sweat.

The invention will now be demonstrated with the help of the following non-limiting examples.

EXAMPLES

Examples A-C, 1: Percentage Flow Rate Reduction Across a Membrane Coated with Antiperspirant Active

Example A

Aluminium chlorohydrate (ACH) aqueous solution (12% w/w solution was used)

Example 1

Complex of zinc acetate dihydrate and 2-amino-1-butanol in 1:1 ratio in ethanolic solution (4% w/w solution was used)

The complex (100 g batch size) was prepared in a process as described below:

Required amount of ligand (Here, 2-amino-1-butanol (2A1B)) was added in 96 g of absolute ethanol taken in a 250 ml volume Scott-Duran stoppered bottle. The mixture was stirred for 10 mins at 600 rpm using a magnetic stirrer, to get it completely dissolved. In this solution, required amount of zinc acetate dihydrate free-flowing powder was added and stirred well at about 600 rpm to get a clear solution. The solution was mixed till all of the zinc acetate dissolved completely. This takes about 15 to 20 minutes at about 25° C. The resulting salt solution was then further stirred for about 6 hours at about 600 rpm. The resulting solution was then ready as an antiperspirant.

Example B

Admixture of zinc acetate dihydrate and 2-amino-1-butanol.

Example C

Zinc lysine complex [Zn (lysine)$_2$. Cl$_2$.2H$_2$O] solution having 1 w % Zn. (as disclosed in US2015/0313821

The above solutions were deposited on a membrane as give below such that the metal deposited was 0.004 g/membrane.

A slightly modified procedure was used for the various examples since they have different solubility and other properties: Example A and C are water soluble and Example 1 is anhydrous while Example B is prepared in hydroalcoholic [1:1] solution.

Procedure Used for Example A:

Whatman cellulose nitrate membranes (AE 100, 12 micron nominal pore size, 50 mm dia.) were coated with required volume of desired % w/v or w/w solution of ACH in water. The coated membranes were taken out and kept in air for 30 mins. Then the membranes were put into a closed chamber having 250 ml 10% (v/v) ammoniacal solution inside to generate an ammoniacal blanketing at 25-30° C. temperature, for 4 hrs to neutralize the active. Then the neutralized membranes were kept in air for 6 hrs to remove excess moisture and were used for flow rate assessment. The membranes were fitted in the Millipore filtration set up and flow rate of artificial sweat under 60 cm constant water bar pressure was measured. The selected water bar pressure corresponds to 5.9 kPa, which is reported as the average secretory pressure of the sweat glands (avg.SPSG)

Procedure Used for Example 1:

Whatman cellulose nitrate membranes (AE 100, 12 micron nominal pore size, 50 mm dia.) were coated with required volume of desired % w/v or w/w solution of zinc complex in ethanol. The coated membranes were taken out and kept in air for 15 mins. Then the membranes were kept into a closed humidity chamber at RH>90% maintained at 25-30° C. temperature for 12 hrs. and then kept in air to remove excess moisture and were used for flow rate assessment.

Procedure for Example B:

Zinc acetate dihydrate was dissolved in water (3.4 g in 100 ml—which will provide 1 wt % elemental zinc) and another solution was prepared dissolving 2-amino-1-butanol in ethanol (1.31 g in 100 ml). Then 8004 (will deposit 0.004 g of Zn/membrane) of each solution was simultaneously added on the Cellulose nitrate membrane (12 micron pore size, 50 mm dia, Whatman AE 100), dried overnight in open air and the membrane was checked for Percentage Flow Rate Reduction.

Procedure for Example C:

0.03 moles of L-Lysine (4.47 g) was dissolved in 96 g of MilliQ water and to it 4 g of Suprapure 30% w/w HCl was added to get a solution of L-Lysine hydrochloride (0.03 moles). To this solution 0.015 mole of ZnO was added (1.24 g of ZnO which will provide 1 g of elemental Zn) slowly and stirred well at 600 rpm on a magnetic stirrer for 12 hrs. The supernatant solution was used as Zinc Lysine complex (ZLC) solution in this study.

Whatman cellulose nitrate membranes (AE 100, 12 micron nominal pore size, 50 mm dia.) were coated with 0.4 ml of ZLC in water, as synthesized above (0.4 ml will give 0.00424 g of Zn). The coated membranes were taken out and kept in air for 30 mins. Then the membranes were put into a closed chamber having 250 ml 10% (v/v) ammoniacal solution inside to generate an ammoniacal blanketing at 25-30 deg. C temperature, for 2 hrs to neutralize the active. Then the neutralized membranes were kept in air for 6 hrs to remove excess moisture and were used for flow rate assessment.

The percentage flow rate reduction was calculated using the equation:

percentage flow rate reduction $$(PFRR) := \frac{[\text{control membrane flow rate(mL/min)} - \text{coated membrane flow rate(mL/min)}]}{[\text{control membrane flow rate(mL/min)}]} \times 100$$

The data on PFRR of the two samples is given in Table-1 below:

TABLE 1

| Example | Avg % PFRR N = 8 |
|---|---|
| A | 66 |
| 1 | 69 |
| B | 5 |
| C | 10 |

The data in Table-1 above indicates that the composition as per the invention (Example 1) provides for slightly better antiperspirant activity as compared to the most commonly used commercial anti perspirant active (Example A). The data also indicates that it is necessary to complex the zinc salt with the β amino alcohol (Example 1) and not simply use an admixture (Example B) in order to get the superior efficacy. The data also indicates that the complex of the present invention (Example 1) provides for vastly superior antiperspirant activity as measured by PFRR as compared to the closest prior art disclosing zinc complexes (Example C).

The invention claimed is:

1. A method of reducing perspiration comprising:
applying an antiperspirant composition onto a skin surface,
wherein the antiperspirant composition comprises:
(i) a complex of a zinc salt with a β amino alcohol; and
(ii) an anhydrous carrier;
wherein the molar ratio of the zinc salt to the β amino alcohol in the antiperspirant composition is from 1:0.5 to 1:3.

2. The method of claim 1, wherein the zinc salt is selected from the group consisting of a chloride, formate, acetate, propionate, gluconate or citrate.

3. The method of claim 1, wherein said β amino alcohol is chosen from mono ethanol amine, diethanol amine, triethanol amine or 2-amino-1-butanol.

4. The method of claim 1, wherein the molar ratio of the zinc salt to the β amino alcohol is from 1:1 to 1:3.

5. The method of claim 1, wherein the complex is dissolved or suspended in an anhydrous solvent.

6. The method of claim 5, wherein the anhydrous solvent is selected from the group consisting of isopropyl alcohol, ethanol, silicone oil or polyhydric alcohol.

7. The method of claim 1, comprising 0.2 to 2% zinc by weight of the composition.

8. The method of claim 6, wherein the polyhydric alcohol is glycerol.

9. The method of claim 1, wherein the composition is delivered as an aerosol.

10. The method of claim 1, wherein the complex is prepared using a process comprising the steps of:
(i) dissolving the β amino alcohol in a volatile alcohol; and
(ii) dissolving therein the zinc salt.

11. The method of claim 10, wherein the dissolving is carried out from about 20° C. to about 40° C.

12. The method of claim 10, wherein the volatile alcohol is ethanol or propanol.

13. The method of claim 10, wherein a polyol is dissolved in the volatile alcohol.

* * * * *